(12) United States Patent
Christie et al.

(10) Patent No.: US 7,719,420 B2
(45) Date of Patent: May 18, 2010

(54) LOCK STATUS NOTIFICATION AND NEXT CASE MEDICATION METHOD, APPARATUS AND CORRESPONDING MEDICATION STORAGE DEVICE

(75) Inventors: Melanie Ann Christie, Butler, PA (US); Jeffrey John Thompson, Allison Park, PA (US); Nicole Nuttall, Cranberry Township, PA (US)

(73) Assignee: McKesson Automation Inc., Cranberry, PA (US)

( * ) Notice: Subject to any disclaimer, the term of this patent is extended or adjusted under 35 U.S.C. 154(b) by 328 days.

(21) Appl. No.: 12/031,254

(22) Filed: Feb. 14, 2008

(65) Prior Publication Data

US 2009/0210089 A1 Aug. 20, 2009

(51) Int. Cl.
*E05B 45/06* (2006.01)
(52) U.S. Cl. .................. 340/542; 700/231
(58) Field of Classification Search .......... 340/542, 340/5.73, 309.16, 309.4; 221/2, 12, 15; 312/215; 700/231, 236, 243
See application file for complete search history.

(56) References Cited

U.S. PATENT DOCUMENTS

| | | | | |
|---|---|---|---|---|
| 3,762,601 | A * | 10/1973 | McLaughlin | 221/2 |
| 4,518,208 | A | 5/1985 | Marder | |
| 4,967,928 | A | 11/1990 | Carter | |
| 5,014,875 | A | 5/1991 | McLaughlin et al. | |
| 5,520,450 | A * | 5/1996 | Colson et al. | 312/215 |
| 5,564,803 | A * | 10/1996 | McDonald et al. | 312/215 |
| 5,905,653 | A * | 5/1999 | Higham et al. | 700/231 |
| 6,011,999 | A | 1/2000 | Holmes | |
| 6,068,156 | A | 5/2000 | Liff et al. | |
| 6,073,834 | A | 6/2000 | Michael et al. | |
| 6,339,732 | B1 | 1/2002 | Phoon et al. | |
| 6,401,991 | B1 * | 6/2002 | Eannone | 221/2 |
| 6,604,019 | B2 * | 8/2003 | Ahlin et al. | 700/231 |
| 6,682,156 | B2 * | 1/2004 | Herrington | 312/215 |
| 6,684,126 | B2 * | 1/2004 | Omura et al. | 700/231 |
| 7,451,583 | B2 * | 11/2008 | Kim | 221/125 |
| 2001/0009398 | A1 * | 7/2001 | Sekura et al. | 221/2 |
| 2002/0013640 | A1 | 1/2002 | Phoon et al. | |

OTHER PUBLICATIONS

Artomick Mediacl Carts (brochure), "*Essential Organization Exceptional Performance*" pp. 1-7.

* cited by examiner

*Primary Examiner*—John A Tweel, Jr.
(74) *Attorney, Agent, or Firm*—Alston & Bird LLP

(57) ABSTRACT

A lock status notification method, apparatus and corresponding medication storage device (e.g., mobile medication dispensing cart, medication cabinet, nurse server, etc.) are provided. In order to generate the notification, a computing device operating on the medication storage device may monitor the status of a manual lock associated with one or more drawers of the medication storage device (e.g., through the use of a sensor associated with the lock). A notification may be generated if it is determined that the medication storage device is unlocked at a certain point in time (e.g., when a user is attempting to log off of an application executing on the computing device). At least one of the drawers of the medication storage device may include a next case medication pocket having an automatic lock and in which medications prepared for the next case or procedure in which the user is participating can be securely stored.

29 Claims, 5 Drawing Sheets

LOCK STATUS NOTIFICATION AND NEXT CASE MEDICATION METHOD, APPARATUS AND CORRESPONDING MEDICATION STORAGE DEVICE

FIELD

Embodiments of the invention relate, generally, to medication storage devices and, in particular, to a technique for ensuring that medications stored in the medication storage device are secure yet readily accessible.

BACKGROUND

One way for doctors, anesthesiologists, nurses, pharmacists, and the like (referred to hereinafter as "healthcare workers") to store, transport and dispense medications to their patients is through the use of a medication storage device (e.g., a mobile medication dispensing cart, a medication cabinet, a nurse server, etc.). In particular, a healthcare worker may have his or her own medication storage device, which stores various medications and/or items or devices used for dispensing or delivering those medications (e.g., syringes, gloves, etc.) throughout a given workday. An example of such a medication storage device may be an anesthesiology cart used by an anesthesiologist for storing all of the medications and dispensing/delivery equipment needed for the procedures (e.g., surgeries) in which he or she is going to participate within a given period of time (e.g., one workday).

In many instances medication storage devices may include controlled substances including, for example, one of various types of narcotics. Given the significant risk involved in association with an unauthorized person obtaining access to these controlled substances, it is very important that adequate security be provided for the medication storage device. In order to provide this security, at least two types of locks associated with the overall medication storage device have been used, each of which having its own set of drawbacks. The first type of lock that is often used is a manual lock that requires the use of a physical key to unlock. One drawback of this technique is that it forces the healthcare worker to carry around the physical key, which can be easily misplaced or stolen. In order to avoid carrying the key and, therefore, potentially losing it, the healthcare worker may be tempted to leave the key in the manual lock on the storage device. This significantly reduces, if not completely abolishes, the security affects of having a lock, thus providing a second drawback to the manual lock.

The second type of lock used by many medication storage devices is an automatic lock, wherein the healthcare worker operating the medication storage device may define a specific period of time after which the storage device will automatically lock. Once locked, the healthcare worker will be forced to manually unlock the storage device again if he or she still needs access to the medications and/or dispensing/delivery items stored in the medication storage device. While this technique eliminates the need for the healthcare worker to carry, and potentially misplace, a physical key, use of an automatic lock has drawbacks of its own. For example, no automatic lock setting appears to satisfy all of the needs of the healthcare worker. In particular, while one procedure, for which the healthcare worker is dispensing medications from the medication storage device, may last only a short period of time (e.g., one hour), another procedure may last significantly longer (e.g., over ten hours). Setting the automatic lock to lock after a short period of time may disrupt longer procedures, while setting the automatic lock to lock after a longer period of time to accommodate those procedures may greatly reduce the security provided by the automatic lock. In addition, healthcare workers that know that the medication storage device will automatically lock after a certain period of time may become dependent upon this functionality and, therefore, even less likely to manually lock the storage device themselves.

In addition to the foregoing, because emergency situations may occur at any moment, the idea of having any lock, whether manual or automatic, on a medication storage device that may prevent the healthcare worker from immediately accessing the needed medications stored within the medication storage device can be unnerving. One solution to this problem has been to have no security at all in relation to the medication storage device. Given the hazards described above with regard to unauthorized access to the controlled substances stored within the medication storage device, this option is less than ideal. A need, therefore, exists for a technique for securing a medication storage device (e.g., mobile medication dispensing cart, medication cabinet, nurse server, etc.) that addresses these, and similar, drawbacks.

Another related issue regarding the dispensing of medications to patients results from the lack of time many healthcare workers have between procedures or cases. In particular, as a result of the extremely quick turnaround time between operating room cases, which can be as little as 12 minutes, anesthesia providers and other healthcare workers often have to draw up or prepare medications for their next case prior to the completion of the current case. In many instances, once the medications (referred to hereinafter as the "next case medications") have been drawn up, they are placed on the top of the anesthesia provider's work surface (e.g., on a mobile medication dispensing cart). As noted above, however, in many instances these medications include controlled substances that should be secured whenever possible. In addition, placing the next case medications on the work surface on which the current case's medications have likely also been placed creates the potential for the medications to be mixed up or confused. A further need, therefore, exists for a technique for ensuring that next case medications are secure and not likely to be confused with the medications of a current case, but that still supports the need to prepare medications in advance.

BRIEF SUMMARY

In general, embodiments of the present invention provide an improvement by, among other things, providing a lock status notification procedure and system whereby the status of a manual, keyless lock associated with a medication storage device (i.e., whether the lock is locked or unlocked) may be monitored, and a notification may be generated if the medication storage device (e.g., mobile medication storage cart, medication cabinet, nurse server, etc.) is unlocked at a certain point in time. For example, a lock status notification may be generated if it is determined that the medication storage device is unlocked after most procedures are typically completed for a given day (e.g., after 6 PM), or when a user operating the medication storage device is attempting to, or has already, logged off of a software application running in association with the medication storage device. According to one embodiment, the time at which a notification may be generated (e.g., the triggering event) may be defined by an administrator associated with the medication storage device. Embodiments of the present invention may provide a further improvement by providing a next case medication pocket within the medication storage device in which the healthcare worker (e.g., the anesthesia provider) can securely place the next case medications that have been drawn up or prepared.

In accordance with one aspect, a method is provided for providing a lock status notification in relation to a medication storage device. In one embodiment, the method may include: (1) receiving a signal indicating that a lock on a medication storage device has been unlocked; (2) determining whether a predetermined event associated with the medication storage device has occurred; (3) determining whether the lock on the medication storage device is still unlocked, if it is determined that the predetermined event associated with the medication storage device has occurred; and (4) generating a notification indicating that the medication storage device is unlocked, if it is determined that the lock on the medication storage device is still unlocked.

In accordance with another aspect, an apparatus is provided for providing a lock status notification in relation to a medication storage device. In one embodiment, the apparatus may include a processor configured to: (1) receive a signal indicating that a lock on a medication storage device has been unlocked; (2) determine whether a predetermined event associated with the medication storage device has occurred; (3) determine whether the lock on the medication storage device is still unlocked, if it is determined that the predetermined event associated with the medication storage device has occurred; and (4) generate a notification indicating that the medication storage device is unlocked, if it is determined that the lock on the medication storage device is still unlocked.

According to yet another aspect, a medication storage device configured to generate a lock status notification is provided. In one embodiment, the medication storage device may include one or more drawers, a lock associated with the one or more drawers, a sensor associated with the lock, and a computing device in electronic communication with the sensor. The computing device of this embodiment may be configured to: (1) receive a signal from the sensor indicating that the lock has been unlocked; (2) determine whether a predetermined event associated with the medication storage device has occurred; (3) determine whether the lock on the medication storage device is still unlocked, if it is determined that the predetermined event associated with the medication storage device has occurred; and (4) generate a notification indicating that the medication storage device is unlocked, if it is determined that the lock on the medication storage device is still unlocked.

In accordance with one aspect, a medication storage device configured to store next case medications is provided. In one embodiment, the medication storage device may include one or more drawers, wherein at least one of the one or more drawers includes one or more pockets. The medication storage device may further include one or more automatic locks associated with respective one or more pockets, and a computing device in electronic communication with the automatic locks. In one embodiment, the computing device may be configured to: (1) receive an instruction to designate at least one of the one or more pockets as a next case medication pocket, wherein the next case medication pocket is configured to store a medication prepared in anticipation of a subsequent case or procedure; (2) receive a request to unlock the next case medication pocket from a user associated with the medication storage device; (3) determine whether the user is authorized to access the next case medication pocket; and (4) transmit a signal to unlock the automatic lock associated with the next case medication pocket, in response to determining that the user is authorized to access the next case medication pocket.

BRIEF DESCRIPTION OF THE SEVERAL VIEWS OF THE DRAWING(S)

Having thus described embodiments of the invention in general terms, reference will now be made to the accompanying drawings, which are not necessarily drawn to scale, and wherein:

DETAILED DESCRIPTION

Figure 1A:
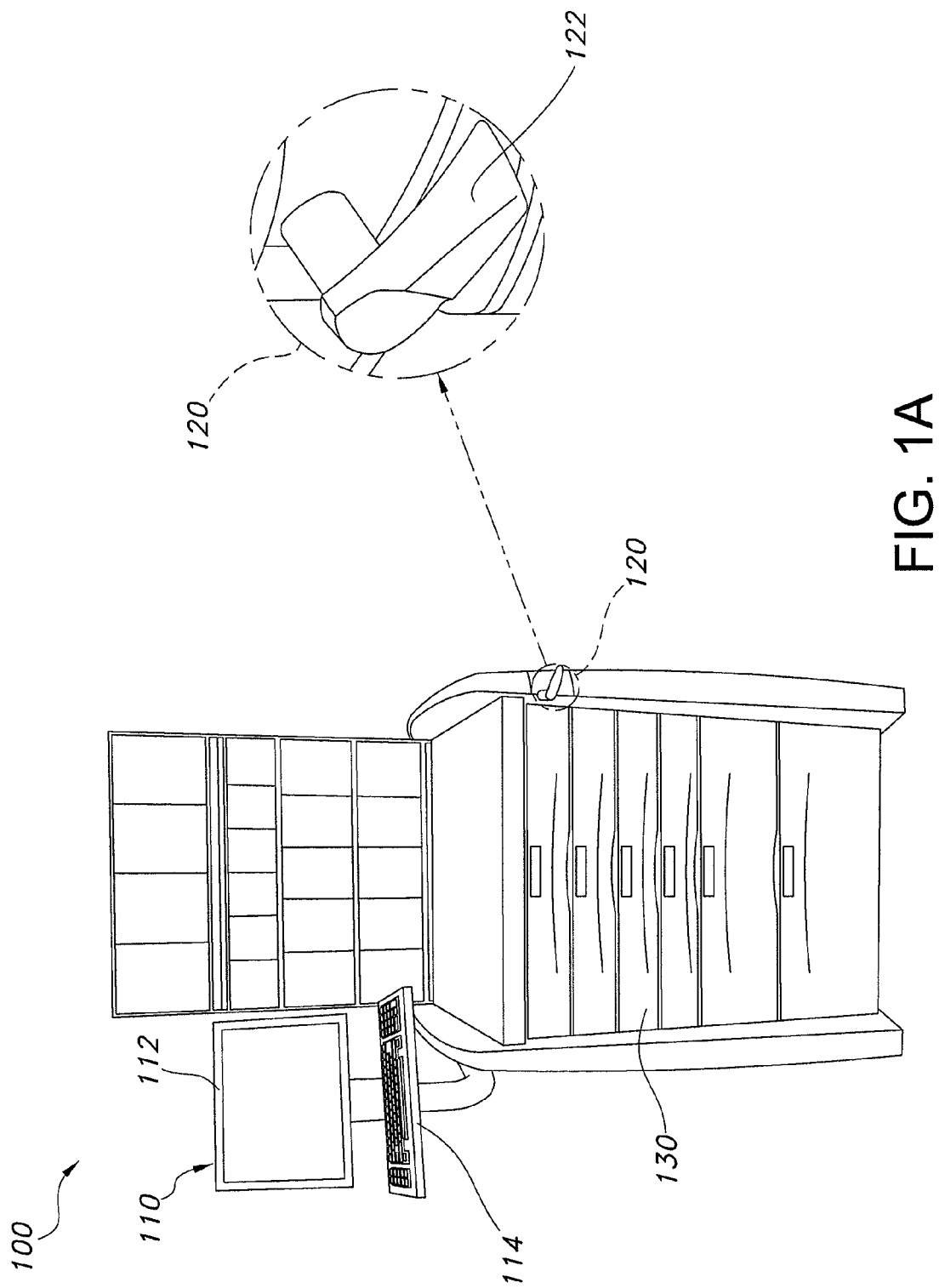
FIGS. 1A and 1B illustrate a mobile medication dispensing cart of one embodiment of the present invention.

Embodiments of the present invention now will be described more fully hereinafter with reference to the accompanying drawings, in which some, but not all embodiments of the inventions are shown. Indeed, embodiments of the invention may be embodied in many different forms and should not be construed as limited to the embodiments set forth herein; rather, these embodiments are provided so that this disclosure will satisfy applicable legal requirements. Like numbers refer to like elements throughout.

Overview:

In general, embodiments of the present invention provide a lock status notification method, apparatus and corresponding medication storage device (e.g., mobile medication dispensing cart, medication cabinet, nurse server, etc.). According to one embodiment, in order to generate the lock status notification, a computing device operating on the medication storage device may monitor the status of a manual, keyless lock associated with one or more drawers of the medication cart including, for example, a manual lever or latch, a biometric lock, a secure identification code-based lock, or the like. This may be done, for example, by transmitting and receiving signals to and from a sensor associated with the lock. A notification may be generated if it is determined that the medication storage device is unlocked at a certain point in time. This may include, for example, when the healthcare worker primarily responsible for the medication storage device is attempting to log off of an application executing on the computing device, in which case the notification may include an alert message displayed on the computing device display screen and, in one embodiment, outputted from speakers associated with the computing device. Alternatively, or in addition, the notification may be generated when it is a time of day before which most procedures or cases would typically have been completed. In this instance, the notification may include a report transmitted to a healthcare administrator associated with the healthcare facility in which the medication storage device is being used, wherein the report includes a summary of the lock status of the medication storage devices used throughout the facility. In yet another embodiment, the notification may be generated when a certain period of time has lapsed since the healthcare worker, or any other individual, has accessed the contents of, or otherwise used, the medication storage device (e.g., a predefined period of inactivity). In any event, according to one embodiment, the time at which the notification is generated (i.e., the triggering event that may cause the notification to be generated) may be defined by an administrator associated with the medication storage device.

In one embodiment, one or more of the drawers of the medication storage device may include one or more pockets for storing different medications and/or devices for dispensing/delivery of the medications. At least one of these pockets may, in one embodiment, be specifically designated as a "next case medication pocket," in which the next case medications, discussed above, may be securely placed. In particular, in one embodiment, each next case medication pocket may include an automatic lock that can only be opened after the healthcare worker verifies that he or she is authorized to open the pocket, and may automatically re-lock when closed and/or after a certain period of time has lapsed.

Based on the foregoing, embodiments of the present invention overcome, among other things, many of the drawbacks described above with regard to medication storage devices. In particular, embodiments of the present invention, while using a manual lock, eliminate the need for the healthcare worker to carry, and potentially misplace, a physical key, since the lock of embodiments may be keyless. In addition, because the locks of embodiments of the present invention do not automatically lock after a predefined amount of time has lapsed since they were unlocked, embodiments of the present invention may satisfy a healthcare worker's need to have access to emergency medications without fear that the medication storage device will automatically lock at a critical moment. On the other hand, embodiments of the present invention may still satisfy the healthcare facility's need to ensure that medications are locked up at the end of the day, or when appropriate supervision is not available. By generating an alert when a healthcare worker is attempting to log off of the medication storage device, embodiments of the present invention remove the likelihood that the healthcare worker will become dependent upon an automatic lock. Embodiments of the present invention further provide a back-up solution if the healthcare worker ignores the warning, by notifying selected personnel if the storage device's lock status does not change after notifying the healthcare worker via the alert message.

In addition, with regard to the next case medication pocket, embodiments of the present invention provide a convenient and efficient way to store a healthcare worker's next case medications that significantly reduces, if not completely eliminates, the risk that the next case medications will be confused with the medications of the current case, as well as the risk that an unauthorized individual may gain access to the next case medications.

Figure 1B:
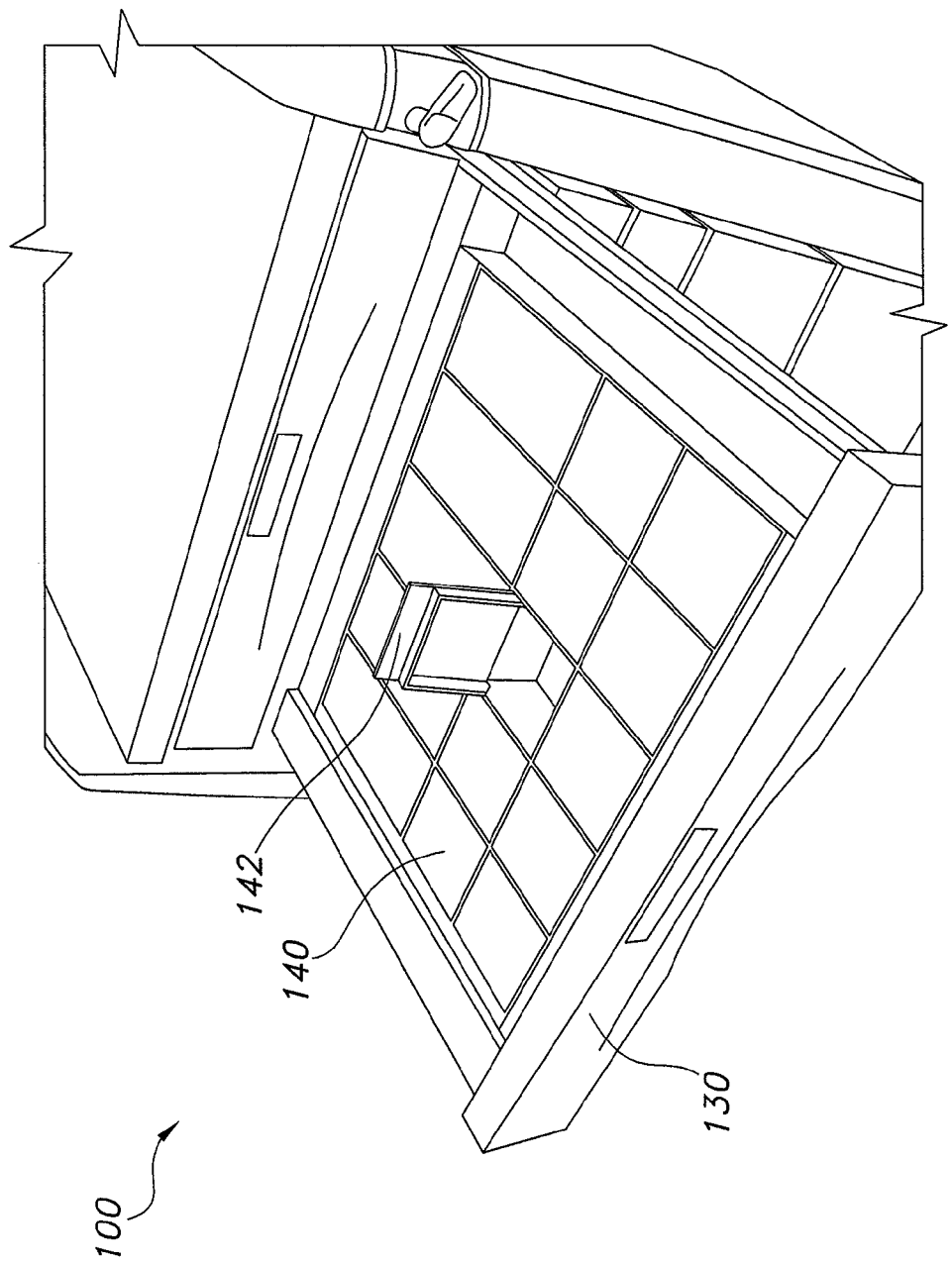

Mobile Medication Dispensing Cart:

Reference is now made to FIGS. 1A and 1B, which provide an example of one type of medication storage device that may be used in conjunction with embodiments of the present invention. In particular, a mobile medication dispensing cart 100 of one embodiment of the present invention is illustrated. As one of ordinary skill in the art will recognize, other types of medication storage devices including, but not limited to, the medication cart 100 shown in FIGS. 1A and 1B, may likewise benefit from embodiments of the present invention. In particular, according to other embodiments, the medication storage device may comprise a medication cabinet, a nurse server, and/or various other types of medication storage equipment or devices. Accordingly, while embodiments herein describe the lock status notification and next case medication processes as being operated in conjunction with a mobile medication dispensing cart 100, embodiments of the present invention are not so limited.

As shown in FIG. 1A, the medication cart 100 may include a computing device 110 (e.g., personal computer (PC), laptop, etc.), which is discussed in more detail below with regard to FIG. 2, and which can be used to access information associated with the medications and dispensing/delivery devices stored in the medication cart, as well as information associated with the patients for which medications may be dispensed from the medication cart at a given point in time. In one embodiment, some or all of this information may be stored locally in memory associated with the computing device 110. In particular, in one embodiment, information associated with the medications and dispensing/delivery devices stored in the medication cart and their location within the medication cart, may be input into the computing device 110 at or near the time when the medication cart is first put into use and automatically updated thereafter as medications are added and/or dispensed. Alternatively, or in addition, some or all of the information may be accessed by the computing device 110, for example via a wireless communication network, on a central server or system associated with the healthcare facility in which the medication cart is being used.

Using the computing device 110, a healthcare worker may request information regarding a patient, as well as input information regarding the medications he or she is dispensing. Accordingly, the computing device 110 may include a display screen 112, a keyboard 114, and/or other input and/or output devices, which are not shown and which may include, for example, a speaker, a barcode reader, a radio frequency identification (RFID) tag reader, and the like.

The medication cart 100 may further include one or more drawers 130 for storing the various medications and dispensing/delivery devices, as well as a manual, keyless lock 120 for locking and unlocking the drawers 130 of the medication cart 100. In the embodiment shown in FIG. 1A, a single lock, which may include, for example, a lever 122, may be used to lock and unlock all of the drawers 130 of the medication cart 100 together. In particular, according to this embodiment, all drawers 130 of the medication cart 100 may be capable of being opened when the lock 120 is unlocked, while none of the drawers 130 may be capable of being opened when the lock 120 is locked. In another embodiment, not shown, separate locks may be used for each of the drawers 130, wherein each drawer is locked and unlocked individually. In addition, while not shown, other types of manual, keyless locks (other than a latch or lever 122) may likewise be used without departing from the spirit and scope of embodiments of the present invention. For example, embodiments of the present invention may include the use of a biometric lock (e.g., using fingerprint recognition), a secure identification code-based lock, and/or any other type of keyless lock.

While not shown, according to embodiments of the present invention, the medication cart 100 may further include one or more electronic sensors associated with the lock 120 and, in one embodiment, each of the drawers 130. In particular, according to one embodiment, an electronic sensor associated with the lock 120, and in electronic communication with the computing device 110, may be configured to monitor the status of the lock (i.e., whether the lock is locked or unlocked) and then provide this information to the computing device 110 for use in generating lock status notifications, discussed in more detail below. For example, the sensor may comprise a position sensor located at or near an axle associated with the lever 122 that is configured to sense the position of the lever 122. Similarly, an electronic sensor associated with a drawer 130 may be configured to monitor whether the drawer 130 is opened or closed and then likewise communicate this information to the computing device 110 for use in a lock status notification.

As shown in FIG. 1B, one or more of the drawers 130 of the medication cart 100 may further include one or more pockets 140 for holding medications and/or dispensing/delivery devices. In one embodiment, each of the pockets 140 may include a lid or cover 142, as well as a corresponding automatic lock (not shown) associated with the lid 142 and in electronic communication with the computing device 110. The automatic lock may cause the pocket 140 to remain locked until the computing device 110 determines that a healthcare worker is authorized to access the pocket 140. When this occurs, the computing device 110 may transmit a signal to the automatic lock instructing the lock to allow the healthcare worker to open the lid 142. Thereafter, the automatic lock may automatically re-lock the pocket 140 when the healthcare worker closes the lid 142 and/or after some predefined amount of time has lapsed. In one embodiment, discussed in more detail below with regard to FIG. 4, at least one of the pockets 140 may be designated as a next case medication pocket for storing the medications drawn up by the healthcare worker in preparation for his or her next procedure or case.

Figure 2:
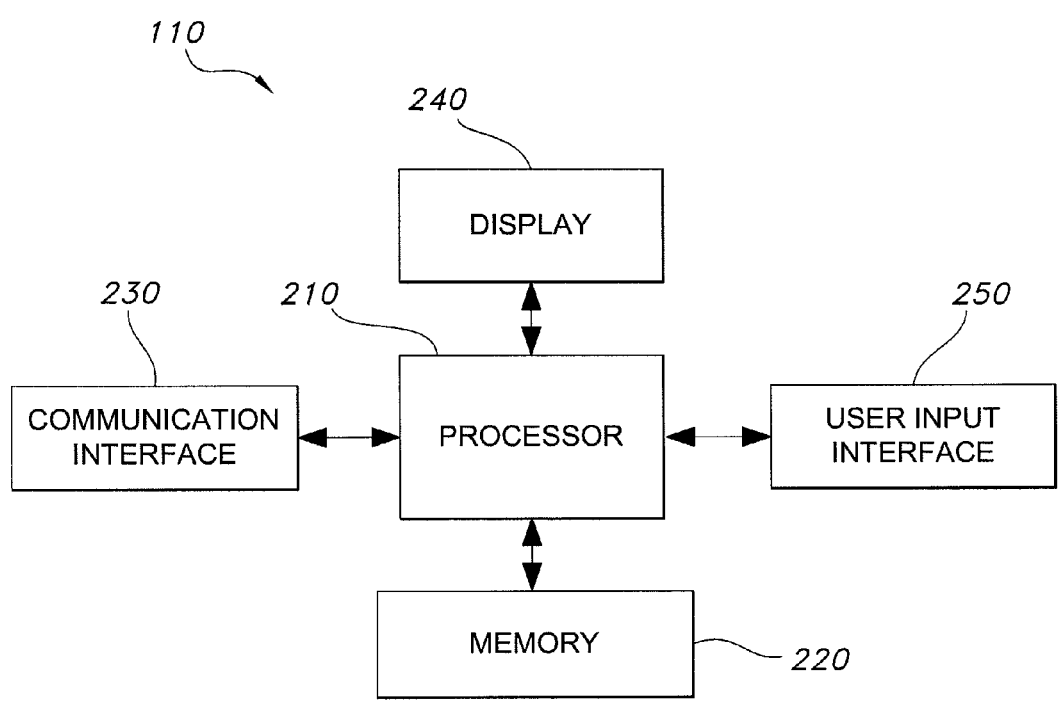
FIG. 2 is a schematic block diagram of an entity capable of operating as a computing device operating on a medication storage device, such as the medication cart, in accordance with embodiments of the present invention.

Referring now to FIG. 2, a block diagram of an entity capable of operating as the computing device 110 operating in association with a medication storage device, such as the mobile medication dispensing cart 100, is shown in accordance with one embodiment of the present invention. The entity capable of operating as the computing device 110 may include various means for performing one or more functions in accordance with embodiments of the present invention, including those more particularly shown and described herein. It should be understood, however, that one or more of the entities may include alternative means for performing one or more like functions, without departing from the spirit and scope of the present invention. As shown, the entity capable of operating as the computing device 110 can generally include means, such as a processor 210 for performing or controlling the various functions of the entity.

In particular, as discussed in more detail below with regard to FIG. 3, according to one embodiment, the processor 210 may be configured to receive a signal (e.g., from the sensor) indicating that the lock 120 on the medication storage device (e.g., medication cart 100) has been unlocked. The processor 210 may thereafter be configured to determine whether a predetermined event associated with the medication storage device has occurred (e.g., whether the healthcare worker is logging off of an application associated with the medication storage device, whether the current time is equal to a predefined time, whether a predefined period of inactivity has lapsed, etc.). If it is determined that the predetermined event has occurred, the processor 210 may be configured to determine whether the lock 120 is still unlocked and to generate a notification that the medication storage device is unlocked, if it is determined that the lock 120 is unlocked.

In addition, as discussed in more detail below with regard to FIG. 4, according to another embodiment, the processor 210 may be configured to receive an instruction to designate at least one of the one or more pockets 140 having an automatic lock as a next case medication pocket. The processor 210 may thereafter be configured to receive a request from a healthcare worker to unlock the next case medication pocket and to transmit a signal to unlock the automatic lock of the next case medication pocket if it is determined that the healthcare worker is authorized to access the next case medication pocket. The processor 210 may further be configured to transmit a signal to relock the automatic lock of the next case medication pocket after a predefined period of time has expired and/or after the healthcare worker has closed a lid 142 associated with the next case medication pocket 140.

In one embodiment, the processor is in communication with or includes memory 220, such as volatile and/or non-volatile memory that stores content, data or the like. For example, the memory 220 typically stores content transmitted from, and/or received by, the entity. Also for example, the memory 220 typically stores software applications, instructions or the like for the processor to perform steps associated with operation of the entity in accordance with embodiments of the present invention. In particular, according to one embodiment of the present invention, the memory may store computer program code or instructions for instructing the processor 210 to perform the steps described above and below with regard to FIGS. 3 and 4.

In addition to the memory 220, the processor 210 can also be connected to at least one interface or other means for displaying, transmitting and/or receiving data, content or the like. In this regard, the interface(s) can include at least one communication interface 230 or other means for transmitting and/or receiving data, content or the like, as well as at least one user interface that can include a display 240 and/or a user input interface 250. The user input interface, in turn, can comprise any of a number of devices allowing the entity to receive data from a user, such as a keypad, a touch display, a joystick or other input device.

Method of Providing a Lock Status Notification

Figure 3:
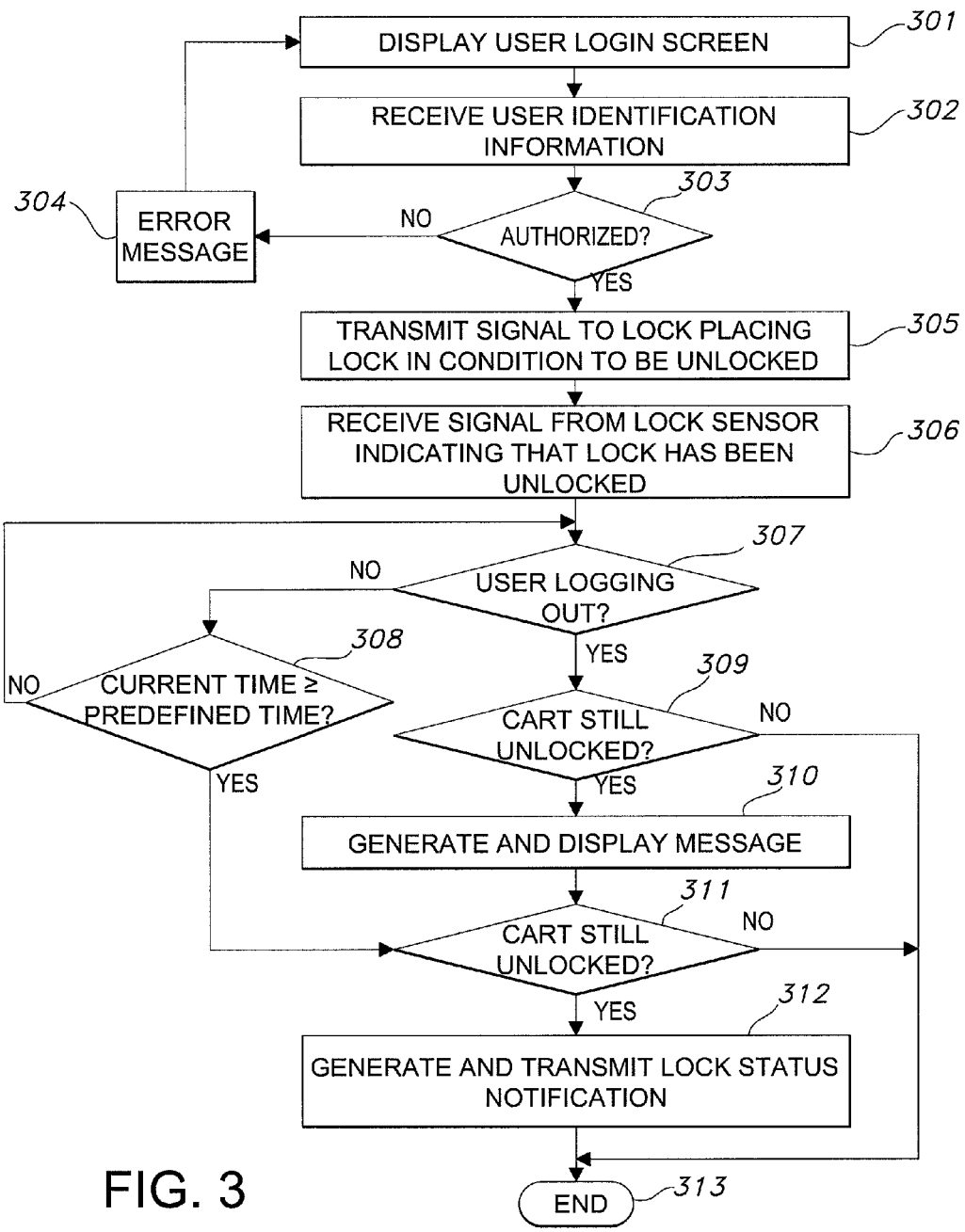
FIG. 3 is flow chart illustrating the process of providing a lock status notification in accordance with an embodiment of the present invention.

Referring now to FIG. 3, the operations are illustrated that may be taken in order to generate a lock status notification in association with a medication storage device (e.g., a mobile medication dispensing cart, medication cabinet, nurse server, etc.) in accordance with embodiments of the present invention. In general, the process may begin when a healthcare worker (e.g., an anesthesia provider) comes into the healthcare facility in order to start his or her shift and logs into a software application operating on his or her medication storage device. In particular, the computing device operating on a medication storage device, and in particular a processor or similar means operating on the computing device, may, at Block 301, display a login screen on the display screen of the computing device. Using the keyboard, or other input device of the computing device, the healthcare worker may input his or her unique identification information, which is received by the computing device (e.g., the processor or similar means operating on the computing device) at Block 302. The unique identification information may include, for example, the healthcare worker's name and social security number, a unique username and password, and/or any information sufficient to verify the healthcare worker's identity.

Based on the information received, the computing device (e.g., processor or similar means) may, at Block 303, determine whether the healthcare worker is authorized, or has the appropriate privileges, to access the medication storage device and its contents. If it is determined that the healthcare worker does not have authorization, the computing device (e.g., processor or similar means) may display an error message on the display screen (at Block 304) followed by the re-displaying of the login screen. If, on the other hand, it is determined that the healthcare worker is authorized to access the medication storage device and its contents, the computing device (e.g., processor or similar means) may transmit a signal to the lock associated with the medication storage device that places the lock in a condition to be manually unlocked by the healthcare worker. (Block 305).

At some point thereafter, the healthcare worker may manually unlock the keyless manual lock of the medication storage device. As discussed above with regard to FIG. 1A, in one embodiment this may be done by pulling on or otherwise changing the position of a lever that serves to lock and unlock all of the drawers, or similar receptacles, of the medication storage device at one time.

As also discussed above, in one embodiment of the present invention, an electronic sensor may be associated with the lock and in electronic communication with the computing device (e.g., with the processor or similar means operating on the computing device). In this embodiment, when the healthcare worker unlocks the keyless manual lock of the medication storage device, the sensor may transmit a signal to the computing device (e.g., processor or similar means), which may receive the signal at Block 306.

Once the lock of the medication storage device has been unlocked, the healthcare worker may be able to freely access the majority of the contents of the medication storage device in order to dispense medications for various patients, as well as to restock the contents of the medication storage device as needed. As discussed in more detail below with regard to FIG. 4, however, some of the drawers may contain one or more pockets that may remain locked until the medications contained in those devices are specifically needed, at which point the healthcare worker may be required to again verify that he or she has authorization to access that pocket, and the computing device (e.g., processor or similar means operating on the computing device) may be required to transmit a signal to unlock an automatic lock associated with that pocket if it is determined that the healthcare worker has authorization.

At this point, the computing device, and in particular a processor or similar means operating on the computing device, may wait for a predetermined event associated with the medication storage device to occur. In particular, according to one embodiment, the computing device (e.g., processor or similar means) may determine, at Block 307, whether the healthcare worker is logging out of the software application associated with the medication storage device (i.e., whether the processor or similar means has received a request from the healthcare worker to log out of the application). If it is determined that the healthcare worker is not logging out of the application, the computing device (e.g., processor or similar means operating on the computing device) may determine, at Block 308, whether the current time is equal to or greater than a predefined time. In particular, in one embodiment, the predefined time may be established by the healthcare worker, or some other party with access to the medication storage device and/or the software application operating on the medication storage device, as a time before which a majority of the cases or procedures being performed by the healthcare worker are likely to have been completed (and, therefore, the medication storage device should be locked). For example, the predefined time may correspond to 6 PM, or a time at which most operating rooms are closed.

If it is determined that the current time is not equal to or greater than the predefined time, the process may return to Block 307 where the computing device (e.g., processor or similar means) again determines whether the healthcare worker is logging off of the application associated with the medication storage device. As described above, the computing device (e.g., processor or similar means) may essentially continue in this loop until either the healthcare worker is logging out of the application associated with the medication storage device or the current time is equal to or greater than the predefined time.

If, on the other hand, it is determined, at Block 308, that the current time is equal to or greater than this predefined time, the computing device (e.g., processor or similar means) may determine, at Block 311, whether the medication storage device is still unlocked. In one embodiment, in order to determine whether the lock of the medication storage device is still unlocked, the computing device (e.g., processor or similar means) may look to a lock status indicator that may be saved in memory associated with the computing device and automatically updated each time a signal is received from the sensor associated with the lock. In this embodiment, the sensor associated with the lock may automatically transmit a signal to the computing device (e.g., processor or similar means operating on the computing device) each time the sensor senses a change in the lock status. The computing device (e.g., processor or similar means) may then use the information received from the sensor to update the lock status indicator. When it is determined that the current time is equal to the predefined time (and/or, as discussed below, when it is determined that the healthcare worker is logging out of the application associated with the medication storage device), the computing device (e.g., processor or similar means) may access this lock status indicator to determine whether the lock of the medication storage device is locked or unlocked. In another embodiment, in order to determine, at Block 311, whether the lock is still unlocked, the computing device (e.g., processor or similar means operating on the computing device) may be required to transmit a signal to the sensor specifically requesting the status of the lock.

If it is determined, at Block 311, that the medication storage device is not still unlocked (i.e., that the healthcare worker has re-locked the drawers of the medication storage device), the process may end. (Block 313). Alternatively, if it is determined that the medication storage device is still unlocked, the computing device (e.g., processor or similar means) may, at Block 312, generate and transmit a lock status notification. In particular, according to one embodiment of the present invention, the lock status notification may include the location of the medication storage device, the name of the healthcare worker assigned to the medication storage device, the time at which the medication storage device was first unlocked, and/or the like. In one embodiment, this notification may be combined with similar notifications associated with other medication storage devices operating throughout the healthcare facility in order to create a summary report of the lock status of all medication storage devices.

As noted above with regard to FIG. 1A, in another embodiment, the medication storage device may further include one or more sensors associated with each of the drawers of the medication storage device. In this embodiment, the sensors may detect whether the drawers of the medication storage device are open or closed and provide this information to the computing device (e.g., processor or similar means) for inclusion in the notification and/or summary report. The notification may indicate which drawers are opened and/or closed, or merely that one of the drawers is open.

The lock status notification generated may be transmitted in any of a number of different manners to any of a number of different recipients in order to notify various individuals associated with the healthcare facility that the medication storage device is unlocked after a certain time of day (e.g., after normal working hours). For example, the notification may be sent to a local or network printer, an email or set of email addresses, a pager, a clinical pharmacy work queue system, and/or the like. Using this information, appropriate individuals may be able to investigate whether the medication storage device should be unlocked and, if not, go lock it.

Returning now to Block 307, if it is determined that the healthcare worker is logging out of the application associated with the medication storage device, the computing device (e.g., processor or similar means operating on the computing device) may determine, for example in any of the manners described above with regard to Block 311, whether the medication storage device is still unlocked. (Block 309). If it is determined that the medication storage device is not still unlocked (i.e., that the healthcare worker has locked his or her medication storage device) the process may end at Block 313.

If, on the other hand, it is determined that the healthcare worker has not re-locked his or her medication storage device prior to attempting to log out of the application operating in association with the medication storage device, the computing device (e.g., processor or similar means operating on the computing device) may generate and display on the computing device display screen an alert message indicating to the healthcare worker that the medication storage device is unlocked. In one embodiment, the alert message may flash and/or include an audible alert tone.

The healthcare worker may then be given a certain amount of time within which to lock the medication storage device (e.g., 2, 5, 15 minutes, etc.). After the predefined amount of time has lapsed, the computing device (e.g., processor or similar means operating on the computing device) may again determine, at Block 311, whether the medication storage device has been locked. If so, the process may end at Block 313. Otherwise, if the healthcare worker has not locked the medication storage device, despite the alert message displayed, the computing device (e.g., processor or similar means operating on the computing device) may generate and transmit a lock status notification. (Block 312).

The lock status notification generated in response to a healthcare worker logging out of the application associated with the medication storage device may or may not contain some or all of the same information as that generated when the current time is equal to the predefined time. For example, in one embodiment, the lock status notification generated in response to the healthcare worker logging out may include an indication of the time at which the healthcare worker logged out of the application, how long it has been, and/or the like. The lock status notification generated in response to the healthcare worker logging out of the application may be transmitted in the same or different manner to the same or different recipients as the lock status notification generated based on the time of day.

While not shown, according to another embodiment of the present invention, in addition to (or instead of) determining whether the current time is equal to or greater than a predefined time and/or whether the healthcare worker is logging off of an application associated with the medication storage device, the computing device (e.g., processor or similar means operating on the computing device) may determine whether a specific period of inactivity has lapsed and, if so, generate and display and/or transmit a lock status notification in the form and manner described above. For example, the computing device (e.g., processor or similar means) may be configured to generate a notification if the lock of the medication storage device is still unlocked 60 minutes after the healthcare worker last dispensed a medication from, or otherwise accessed, the medication storage device. According to embodiments of the present invention, the events that may generate a notification and the form and manner in which the notification is generated, displayed and/or transmitted may be configured by an administrator associated with the medication storage device.

Method of Providing a Next Case Medication Pocket

Figure 4:
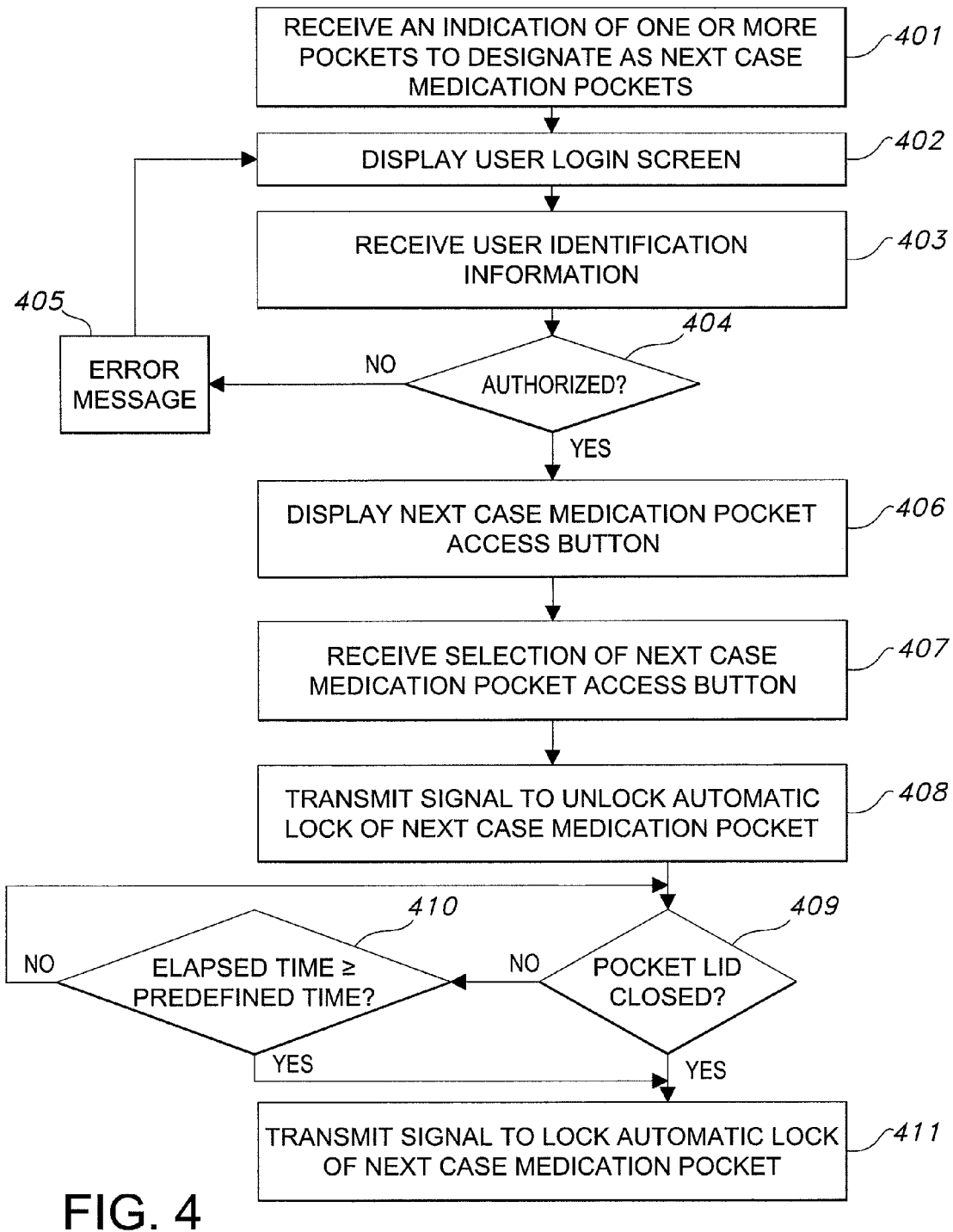
FIG. 4 is a flow chart illustrating the process of designating and using at least one of a plurality of pockets within the medication storage device as a next case medication pocket in accordance with embodiments of the present invention.

Referring now to FIG. 4, the operations are illustrated that may be taken in order to designate and use one or more pockets of the medication storage device (e.g., medication dispensing cart, medication cabinet, nurse server, etc.) as a next case medication pocket. As shown, the process may begin, at Block 401, when the computing device of the medication storage device, and in particular a processor or similar means operating on the computing device, receives an indication of one or more pockets to designate as next case medication pockets. In particular, the healthcare worker, an administrator associated with the healthcare facility, or some other individual, may specifically designate the contents of at least some of the drawers and pockets of the medication storage device. This information may be stored in memory on the computing device and/or in a central database accessible by the computing device (e.g., via a wired or wireless communication network). When designating the contents of the drawers and pockets of the medication storage device, the individual may further designate one or more of the pockets as being used for next case medications. This may prevent those pockets from ever being assigned a medication and/or dispensing/delivery device to store. In one embodiment, only someone having the necessary credentials or privileges may be capable of configuring the next case medication pocket(s) of the medication storage device.

At some point thereafter, a healthcare worker may log on to an application associated with the medication storage device, for example in the manner described above with regard to FIG. 3. In particular, the computing device (e.g., processor or similar means) may display a login screen (at Block 402), receive unique identification information associated with the healthcare worker (at Block 403), and determine whether the healthcare worker is qualified to access the contents of the medication storage device (at Block 404). If the healthcare worker is not qualified, the computing device (e.g., processor or similar means) may display an error message (at Block 405), followed by the login screen. If, on the other hand, the healthcare worker is qualified, the computing device (e.g., processor or similar means operating on the computing device) may enable the healthcare worker to enter the application associated with the medication storage device, as well as access the contents of the medication storage device (discussed above).

In addition, according to one embodiment of the present invention, if the computing device (e.g., processor or similar means operating on the computing device) determines that the healthcare worker is authorized, the computing device (e.g., processor or similar means) may display a button on the computing device display screen that corresponds to the pocket designated as the next case medication pocket. (Block 406). The healthcare worker may use this button to indicate to the computing device that he or she would like to access the next case medication pocket. When the computing device (e.g., processor or similar means operating on the computing device) receives a selection of the displayed button from the healthcare worker (at Block 407), the computing device (e.g., processor or similar means) may transmit a signal to unlock the automatic lock associated with the next case medication pocket (at Block 408).

As described above, the healthcare worker may use the next case medication pocket to store medications that he or she has drawn up in preparation for the next case or procedure in which the healthcare worker is going to participate. This may be necessary given the short period of time between procedures or cases. By using the next case medication pocket, the healthcare worker is able to securely store the next case medications in an area that will prevent the next case medications from being confused with the medications of the current case or procedure, as well as a locked place where unauthorized individuals cannot access it.

The foregoing steps (i.e., Blocks 407 and 408) may be performed when the healthcare worker is first placing the next case medications within the next case medication pocket, as well as when the healthcare worker is retrieving the next case medications from the next case medication pocket for use in a procedure. According to one embodiment, information associated with, for example, who accessed the next case medication pocket(s) (e.g., the healthcare worker's unique identification information, etc.), when they accessed the next case medication pocket(s), which next case medication pocket they accessed (assuming there is more than one), what they did (e.g., stored or retrieved a next case medication, what medication was stored or retrieved, etc.), and/or the like may be stored in memory associated with or accessible by the computing device and later accessed and retrieved.

Once the next case medication pocket has been unlocked and the user has opened the next case medication pocket to either store or retrieve the next case medication, the computing device (e.g., processor or similar means operating on the computing device) may periodically check to see if the healthcare worker has closed the next case medication pocket (e.g., closed the lid of the pocket). (Block 409). If not, the computing device (e.g., processor or similar means) may determine whether a predefined period of time has elapsed since the pocket was unlocked. (Block 410). If the predefined period of time has not elapsed, the computing device (e.g., processor or similar means) may again check to see if the pocket lid has been closed, or the next case medication pocket has otherwise been closed. The computing device (e.g., processor or similar means) may continue in this loop until either the next case medication pocket is closed or the predefined period of time has lapsed. When either the next case medication pocket has been closed (as determined in Block 409), or the elapsed time is greater than or equal to the predefined time (as determined in Block 410), the computing device (e.g., processor or similar means) may transmit a signal to the automatic lock of the next case medication pocket in order to relock the next case medication pocket.

CONCLUSION

As described above and as will be appreciated by one skilled in the art, embodiments of the present invention may be configured as a method, apparatus or medication storage device. Accordingly, embodiments of the present invention may be comprised of various means including entirely of hardware, entirely of software, or any combination of software and hardware. Furthermore, embodiments of the present invention may take the form of a computer program product on a computer-readable storage medium having computer-readable program instructions (e.g., computer software) embodied in the storage medium. Any suitable computer-readable storage medium may be utilized including hard disks, CD-ROMs, optical storage devices, or magnetic storage devices.

Embodiments of the present invention have been described above with reference to block diagrams and flowchart illustrations of methods, apparatuses (i.e., systems) and computer program products. It will be understood that each block of the block diagrams and flowchart illustrations, and combinations of blocks in the block diagrams and flowchart illustrations, respectively, can be implemented by various means including computer program instructions. These computer program instructions may be loaded onto a general purpose computer, special purpose computer, or other programmable data processing apparatus, such as processor 210 discussed above with reference to FIG. 2, to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus (e.g., processor 210 of FIG. 2) to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Many modifications and other embodiments of the inventions set forth herein will come to mind to one skilled in the art to which these embodiments of the invention pertain having the benefit of the teachings presented in the foregoing descriptions and the associated drawings. Therefore, it is to be understood that the embodiments of the invention are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method comprising:
   receiving a signal indicating that a lock on a medication storage device has been unlocked;
   determining whether a predetermined event associated with the medication storage device has occurred;
   determining whether the lock on the medication storage device is still unlocked, if it is determined that the predetermined event associated with the medication storage device has occurred; and
   generating a notification indicating that the medication storage device is unlocked, if it is determined that the lock on the medication storage device is still unlocked.

2. The method of claim 1, wherein receiving a signal indicating that a lock on a medication storage device has been unlocked comprises receiving the signal from a sensor associated with the lock.

3. The method of claim 2, wherein determining whether the lock on the medication storage device is still unlocked comprises:
  transmitting a request to the sensor for a status of the lock; and
  receiving, in response, an indication of whether the lock is locked or unlocked.

4. The method of claim 2, wherein determining whether the lock on the medication storage device is still unlocked comprises accessing a lock status indicator associated with the lock, wherein the lock status indicator is updated each time a signal is received from the sensor associated with the lock.

5. The method of claim 1 further comprising:
  receiving a request to log into an application associated with the medication storage device, said request comprising user identification information associated with a user;
  determining whether the user is authorized to access the medication storage device based at least in part on the user identification information; and
  transmitting a signal to the lock on the medication storage device, said signal enabling the lock to be manually unlocked by the user, if it is determined that the user is authorized.

6. The method of claim 5, wherein determining whether a predetermined event associated with the medication storage device has occurred comprises determining whether the user has transmitted a request to log out of the application.

7. The method of claim 6, wherein the notification comprises an alert message, and wherein the method further comprises:
  displaying the alert message on a display screen associated with the medication storage device.

8. The method of claim 7, wherein the alert message comprises an audio component.

9. The method of claim 7 further comprising:
  determining whether the lock on the medication storage device is still unlocked after a predetermined period of time after displaying the alert message on the display screen;
  generating a second notification; and
  transmitting the second notification to an electronic device.

10. The method of claim 1, wherein determining whether a predetermined event associated with the medication storage device has occurred comprises determining whether a current time is substantially equal to a predefined time.

11. The method of claim 10, wherein the notification comprises a summary of a lock status of one or more medication storage devices, and wherein the method further comprises:
  transmitting the notification to an electronic device.

12. The method of claim 1 further comprising:
  determining if one or more drawers of the medication storage device are open, wherein the notification further indicates whether one or more drawers are open.

13. The method of claim 1, wherein determining whether a predetermined event associated with the medication storage device has occurred comprises determining whether a predefined period of inactivity has lapsed since receiving the signal indicating that a lock on the medication storage device has been unlocked.

14. The method of claim 1, wherein the predetermined event is defined by an administrator associated with the medication storage device.

15. An apparatus comprising:
  a processor configured to:
    receive a signal indicating that a lock on a medication storage device has been unlocked;
    determine whether a predetermined event associated with the medication storage device has occurred;
    determine whether the lock on the medication storage device is still unlocked, if it is determined that the predetermined event associated with the medication storage device has occurred; and
    generate a notification indicating that the medication storage device is unlocked, if it is determined that the lock on the medication storage device is still unlocked.

16. An apparatus of claim 15 further comprising:
  a sensor associated with the lock and in electronic communication with the processor, wherein in order to receive a signal indicating that a lock on a medication storage device has been unlocked, the processor is further configured to receive the signal from the sensor.

17. The apparatus of claim 15, wherein in order to determine whether a predetermined event associated with the medication storage device has occurred, the processor is further configured to determine whether a user associated with the medication storage device has transmitted a request to log out of an application associated with the medication storage device.

18. The apparatus of claim 17, wherein the notification comprises an alert message, said apparatus further comprising:
  a display device in electronic communication with the processor, said display device configured to display the alert message.

19. The apparatus of claim 15, wherein in order to determine whether a predetermined event associated with the medication storage device has occurred, the processor is further configured to determine whether a current time is substantially equal to a predefined time.

20. The apparatus of claim 19, wherein the notification comprises a summary of a lock status of one or more medication storage devices, and wherein the processor is further configured to:
  transmit the notification to an electronic device.

21. A medication storage device comprising:
  one or more drawers;
  a lock associated with the one or more drawers;
  a sensor associated with the lock; and
  a computing device in electronic communication with the sensor, said computing device configured to:
    receive a signal from the sensor indicating that the lock has been unlocked;
    determine whether a predetermined event associated with the medication storage device has occurred;
    determine whether the lock on the medication storage device is still unlocked, if it is determined that the predetermined event associated with the medication storage device has occurred; and
    generate a notification indicating that the medication storage device is unlocked, if it is determined that the lock on the medication storage device is still unlocked.

22. The medication storage device of claim 21, wherein in order to determine whether a predetermined event associated with the medication storage device has occurred, the computing device is further configured to determine whether a user associated with the medication storage device has transmitted a request to log out of an application associated with the medication storage device.

23. The medication storage device of claim 22, wherein the notification comprises an alert message, said medication storage device further comprising:

a display device in electronic communication with the computing device, said display device configured to display the alert message.

24. The medication storage device of claim 21, wherein in order to determine whether a predetermined event associated with the medication storage device has occurred, the computing device is further configured to determine whether a current time is substantially equal to a predefined time.

25. The medication storage device of claim 24, wherein the notification comprises a summary of a lock status of one or more medication storage devices, and wherein the computing device is further configured to transmit the notification to an electronic device.

26. A medication storage device comprising:

one or more drawers, at least one of the one or more drawers comprising one or more pockets;

one or more automatic locks associated with respective one or more pockets; and a computing device in electronic communication with the one or more automatic locks, said computing device configured to:

receive an instruction to designate at least one of the one or more pockets as a next case medication pocket, said next case medication pocket configured to store a medication prepared in anticipation of a subsequent case or procedure;

receive a request to unlock the next case medication pocket from a user associated with the medication storage device;

determine whether the user is authorized to access the next case medication pocket; and transmit a signal to unlock the automatic lock associated with the next case medication pocket, in response to determining that the user is authorized to access the next case medication pocket.

27. The medication storage device of claim 26, wherein the computing device is further configured to:

transmit a signal to relock the automatic lock associated with the next case medication pocket after a predefined period of time has expired.

28. The medication storage device of claim 26, wherein the computing device is further configured to:

receive a signal indicating that the next case medication pocket has been closed; and transmit a signal to relock the automatic lock associated with the next case medication pocket in response to receiving the signal.

29. The medication storage device of claim 26, wherein the computing device is further configured to:

store user identification information associated with the user from whom the request was received; and store, in association with the user identification information, a time at which the request was received.

* * * * *